United States Patent
Chen

(10) Patent No.: US 10,806,636 B2
(45) Date of Patent: Oct. 20, 2020

(54) WATER-ABSORBENT CORE PRODUCTION SYSTEM

(71) Applicant: Jianhui Chen, Guangdong Province (CN)

(72) Inventor: Jianhui Chen, Guangdong Province (CN)

( * ) Notice: Subject to any disclaimer, the term of this patent is extended or adjusted under 35 U.S.C. 154(b) by 0 days.

(21) Appl. No.: 16/047,631

(22) Filed: Jul. 27, 2018

(65) Prior Publication Data
US 2019/0029892 A1    Jan. 31, 2019

(30) Foreign Application Priority Data

Jul. 28, 2017   (CN) .......................... 2017 1 0632806

(51) Int. Cl.
*A61F 13/00*    (2006.01)
*B65H 35/00*    (2006.01)
(Continued)

(52) U.S. Cl.
CPC .. *A61F 13/15764* (2013.01); *A61F 13/15658* (2013.01); *A61F 13/15723* (2013.01);
(Continued)

(58) Field of Classification Search
CPC .......... A61F 13/15764; A61F 13/15658; A61F 13/15723; A61F 13/15804; A61F 13/53;
(Continued)

(56) References Cited

U.S. PATENT DOCUMENTS

| 6,540,853 B1* | 4/2003 | Suzuki .................. D21H 21/22 156/181 |
| 2008/0280520 A1 | 11/2008 | Schmidt et al. |
| 2017/0172810 A1 | 6/2017 | Van De Maele |

FOREIGN PATENT DOCUMENTS

| CN | 101929082 A | 12/2010 |
| CN | 201850469 U | 6/2011 |

(Continued)

OTHER PUBLICATIONS

European Search Report related to Application No. EP 18186109.7 dated Nov. 6, 2018.
(Continued)

*Primary Examiner* — Linda L Gray
(74) *Attorney, Agent, or Firm* — Miller, Matthias & Hull LLP

(57) ABSTRACT

A production system of a water-absorbent core. The supplying component thereof is configured to convey the fluffy cotton to the starting end of the transmission component, and the plurality of outlets of the supplying component for conveying the mixture of the fluff pulp and the hot-melt fibers to the transmission component are all located in the middle portion of the transmission component, the feeding port for conveying the super absorbent polymer to the transmission component and the outlets are arranged alternately along the transmitting direction of the transmission component, and each feeding port is located between the two outlets; the vacuum adsorption device can cause the mixture to be absorbed on the transmission component; the hot air penetration device performs hot air penetration treatment on the laminate; and the ultrasonic cutting device of the slitting mechanism is configured to ultrasonically cut the laminate after the hot air penetration treatment.

20 Claims, 3 Drawing Sheets

(51) Int. Cl.
  *B65H 39/00* (2006.01)
  *A61L 15/00* (2006.01)
  *B29C 65/00* (2006.01)
  *A61F 13/15* (2006.01)
  *A61F 13/53* (2006.01)
  *B65H 35/02* (2006.01)
  *B65H 39/14* (2006.01)
  *B29C 65/74* (2006.01)
  *A61L 15/18* (2006.01)

(52) U.S. Cl.
  CPC ........ *A61F 13/15804* (2013.01); *A61F 13/53* (2013.01); *B65H 35/02* (2013.01); *B65H 39/14* (2013.01); *A61L 15/18* (2013.01); *B29C 65/745* (2013.01); *B29C 65/7443* (2013.01); *B29C 65/7455* (2013.01); *B65H 2801/57* (2013.01); *Y10T 156/1054* (2015.01); *Y10T 156/1067* (2015.01); *Y10T 156/1313* (2015.01)

(58) Field of Classification Search
  CPC ... B65H 35/02; B65H 39/14; Y10T 156/1313; Y10T 156/1054; Y10T 156/1067; B29C 65/7443; B29C 65/745; B29C 65/7455
  See application file for complete search history.

(56) References Cited

FOREIGN PATENT DOCUMENTS

| | | |
|---|---|---|
| CN | 202934649 U | 5/2013 |
| CN | 103666367 A | 3/2014 |
| CN | 204766192 U | 11/2015 |
| CN | 204839969 U | 12/2015 |
| CN | 205241892 U | 5/2016 |
| CN | 106137555 A | 11/2016 |
| CN | 208525235 U | 2/2019 |
| EP | 2540266 A1 | 1/2013 |
| WO | WO 2012170338 A1 | 12/2012 |

OTHER PUBLICATIONS

Chinese Office Action related to Application No. 201710632806.6; reported on Mar. 4, 2020.

* cited by examiner

WATER-ABSORBENT CORE PRODUCTION SYSTEM

CROSS-REFERENCE TO RELATED APPLICATION

This application claims priority to Chinese Patent Application No. 2017106328066, entitled "PRODUCTION SYSTEM OF A WATER-ABSORBENT CORE" filed Jul. 28, 2017, the content of which is expressly incorporated by reference herein in its entirety.

TECHNICAL FIELD

The disclosure relates to the field of production of sanitary articles, in particular to a production system of a water-absorbent core.

BACKGROUND

Typically, diapers, sanitary napkins, and the like are required to have a good water absorbing performance, and therefore are generally provided with a water-absorbent core. At present, there are mainly two modes of production of absorbent core, one of which is on-line mixing of fluff pulp and polymer absorbent resin (SUPER ABSORBENT POLYMER, SAP), although the cost is low, the products spread fast and the multi-absorption effect is favorable, still, after the water-absorbent resin is swelled after absorbent water, it is vulnerable to rupture and flock, which not only affects the comfortableness, but also affects the effective usage time. In order to avoid flocking, manufacturers reduce the amount of water-absorbent resin, but the absorption capacity and use time of the product is also reduced. Another way is to fix the SAP with a fluffy non-woven fabric, and use hot-melt composite puffing paper (or dust-free paper, non-woven fabric, etc.) on the upper and lower sides respectively, and obtain the product after winding and slitting. Although the connectivity of the absorbent core obtained by this approach is improved yet still insufficient. The polymer layer is obviously stratified after water swelling and swelling. The single-point multiple water absorption performance is poor, the expansion linearity is slow, and side/back leakage problems are likely to happen.

At present, for the production of the water-absorbent core of the multi-layer structure, each layer structure is usually formed by multiple molding and then each layer structure is laminated, which requires multiple production, which not only consumes labor, but also leads to low production efficiency.

SUMMARY

Accordingly, it is necessary to provide production system of a water-absorbent core, and the water-absorbent core prepared by the production system is not easy to be stratified after the water-absorbent resin absorbs water and has a good water-absorbent effect, and can effectively improve the production efficiency and save human power.

A production system of a water-absorbent core includes: a manufacturing mechanism and a slitting mechanism, the manufacturing mechanism includes a transmission component, a supplying component, a supplying component, a feeding component, a vacuum adsorption device, and a hot air penetration device:

the supplying component is configured to convey fluffy cotton to a starting end of the transmission component;

the supplying component is configured to convey a mixture of fluff pulp and hot-melt fibers to the transmission component, the transmission component has a plurality of outlets, and the plurality of outlets are located in a middle portion of the transmission component;

the feeding component is configured to convey a super absorbent polymer to the transmission component, the feeding component has a plurality of feeding ports, the feeding ports and the plurality of outlets are arranged alternately along a transmitting direction of the transmission component, and each feeding port is located between two of the outlets;

the transmission component is configured to drive the mixture of the fluff pulp and the hot-melt fibers, the fluffy cotton, and the super absorbent polymer to move in the transmitting direction of the transmission component, such that the mixture of the fluff pulp and the hot-melt fibers, and the polymeric water-absorbent resin are laminated on the fluffy cotton to form a laminate, and the transmission component is further configured to convey the laminate into the hot air penetration device;

the vacuum adsorption device is disposed adjacent to the transmission component, and a position of the vacuum adsorption device corresponds to a position of the plurality of outlets, such that the mixture of fluff pulp and hot-melt fibers can be absorbed on the transmission component;

the hot air penetration device is disposed adjacent to a terminal end of the t transmission component, and the hot air penetration device is configured to perform a hot air penetration treatment to the laminate; and the slitting mechanism includes an ultrasonic cutting device configured to ultrasonically cut the laminate after the hot air penetration treatment and fuse hot-melt fibers at a cut portion of the laminate.

Since the supplying component of the production system of a water-absorbent core can feed fluffy cotton to the starting end of the transmission component, the plurality of outlets of the supplying component configured to convey the mixture of fluff pulp and hot-melt fibers onto the transmission component are located in the middle portion of the transmission component, the plurality of feeding ports of the feeding component configured to convey the super absorbent polymer to the transmission component and the plurality of outlets are arranged alternately along the transmitting direction of the transmission component, and each feeding port is located between two of the outlets, and the vacuum adsorption device is disposed adjacent to the transmission component. The position of the vacuum adsorption device corresponds to the positions of the plurality of outlets such that the mixture of the fluff pulp and the hot-melt fibers can be absorbed on the transmission component such that, with the conveying effect of the transmission component, the mixture of the hot-melt fibers and the fluff pulp output from the outlet and the super absorbent polymer output from the feeding port can drop onto the fluffy cotton conveyed at the starting end of the transmission component to form a laminate according to the arrangement sequence of the outlets and the feeding ports. And the mixture of the pulverescent hot-melt fibers and fluff pulp outputted from the outlet can be absorbed on the fluffy cotton on the transmission component under the suction of the vacuum adsorption device. And each super absorbent polymer layer of the formed laminate is sandwiched between two layers of the mixture of the hot-melt fibers and fluff pulp. The laminate is further conveyed by the transmission component to the hot air penetration device to perform hot air penetration treatment to the laminate to melt the hot-melt fibers, thereby bonding the fluffy cotton, each super absorbent polymer layer, each hot-melt fibers and fluff pulp mixture layer together to shape the laminate. This not only can realize the automatic lamination of layers and the automatic hot air penetration treatment of the laminates, effectively improve the production efficiency and save manpower, but also can connect the layers together well, so that the layers of the absorbent core have better connectivity and the stratification problem caused by water swelling of the absorbent resin is reduced. In addition, since each super absorbent polymer is located between that two layers of mixture of the hot-melt fibers and the fluff pulp, the fluff pulp in each layer of the mixture of the hot-melt fibers and the fluff pulp can provide the flow guide effect, thereby providing each layer of the mixture of hot-melt fibers and the fluff pulp with a better diffusibility to improve the diffusion and absorption of the water-absorbent core. At the same time, the ultrasonic cutting device of the slitting mechanism ultrasonically cuts the laminate after the hot air penetration treatment to obtain the water-absorbent core, so that not only the laminate can be cut, but also the hot-melt fibers of each layer of the laminate can be fused again. Thereby further increasing the connectivity between the layers of the water-absorbent core and functioning as an edge seal while cutting.

DETAILED DESCRIPTION OF THE EMBODIMENTS

Figure 1:
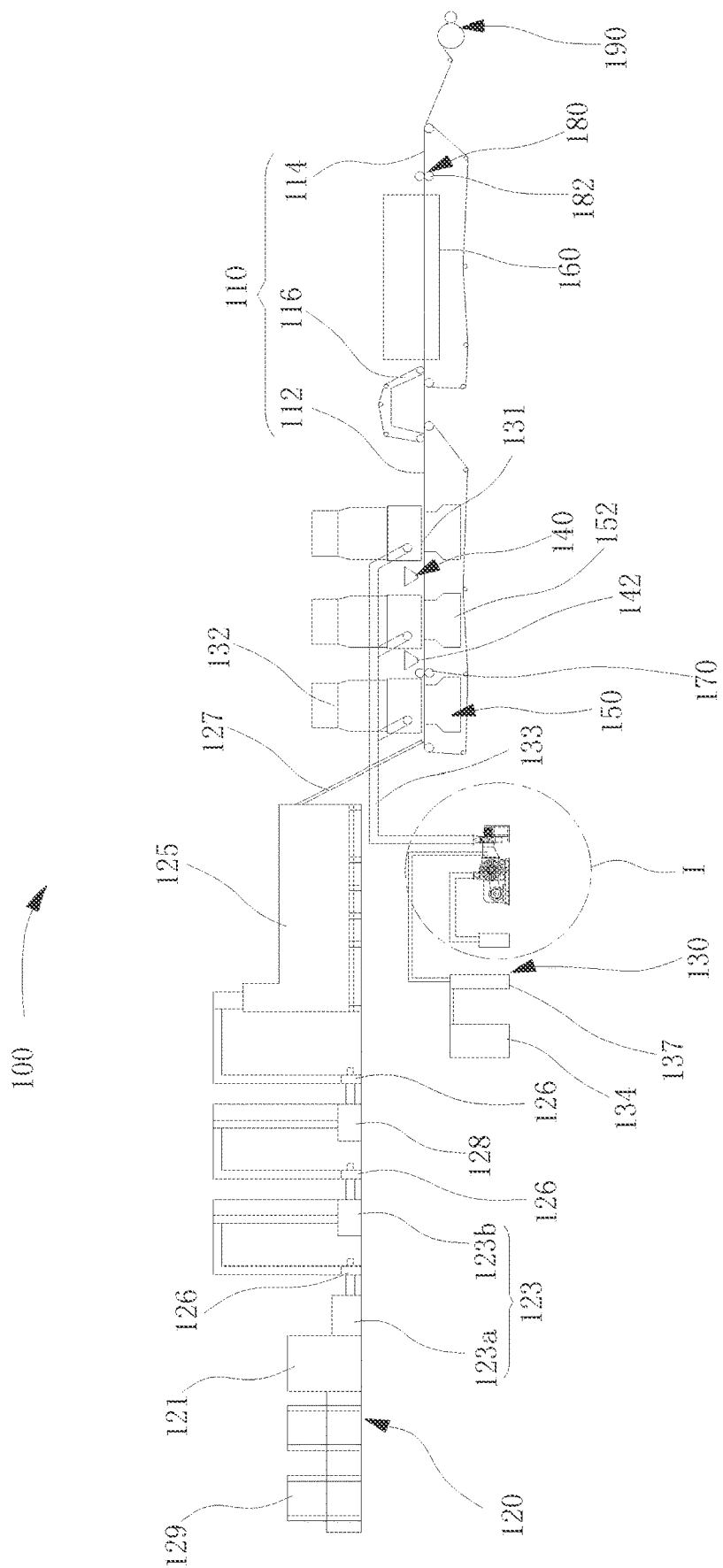
FIG. 1 is a schematic view of a manufacturing mechanism of a production system of a water-absorbent core according to an embodiment.

Embodiments of the disclosure are described more comprehensively hereinafter with reference to the accompanying drawings. Preferable embodiments are presented in the drawings. The various embodiments of the disclosure may, however, be embodied in many different forms and should not be construed as limited to the embodiments set forth herein. Rather, these embodiments are provided so that this disclosure will be thorough and complete, and will fully convey the scope of the disclosure to those skilled in the art.

It should be understood that when an element is defined as "fixed to" another element, it is either directly on an element or indirectly on an element with a mediating element. When an element is considered being "connected" to another element, it is either directly connected to an element or indirectly connected to an element with a mediating element. The terms used in the disclosure such as "upright", "horizontal", "left", "right" and other wordings are intended for descriptive purpose only.

Unless otherwise defined, all terms used herein have the same meaning as commonly understood by one of ordinary skill in the art to which this disclosure belongs. The terms used in the specification of the present invention is for the purpose of describing the embodiments of the present invention, as opposed to limiting thereto. The language "and/or" used in the disclosure refers to any and all combinations of the one or multiple items listed.

Figure 2:
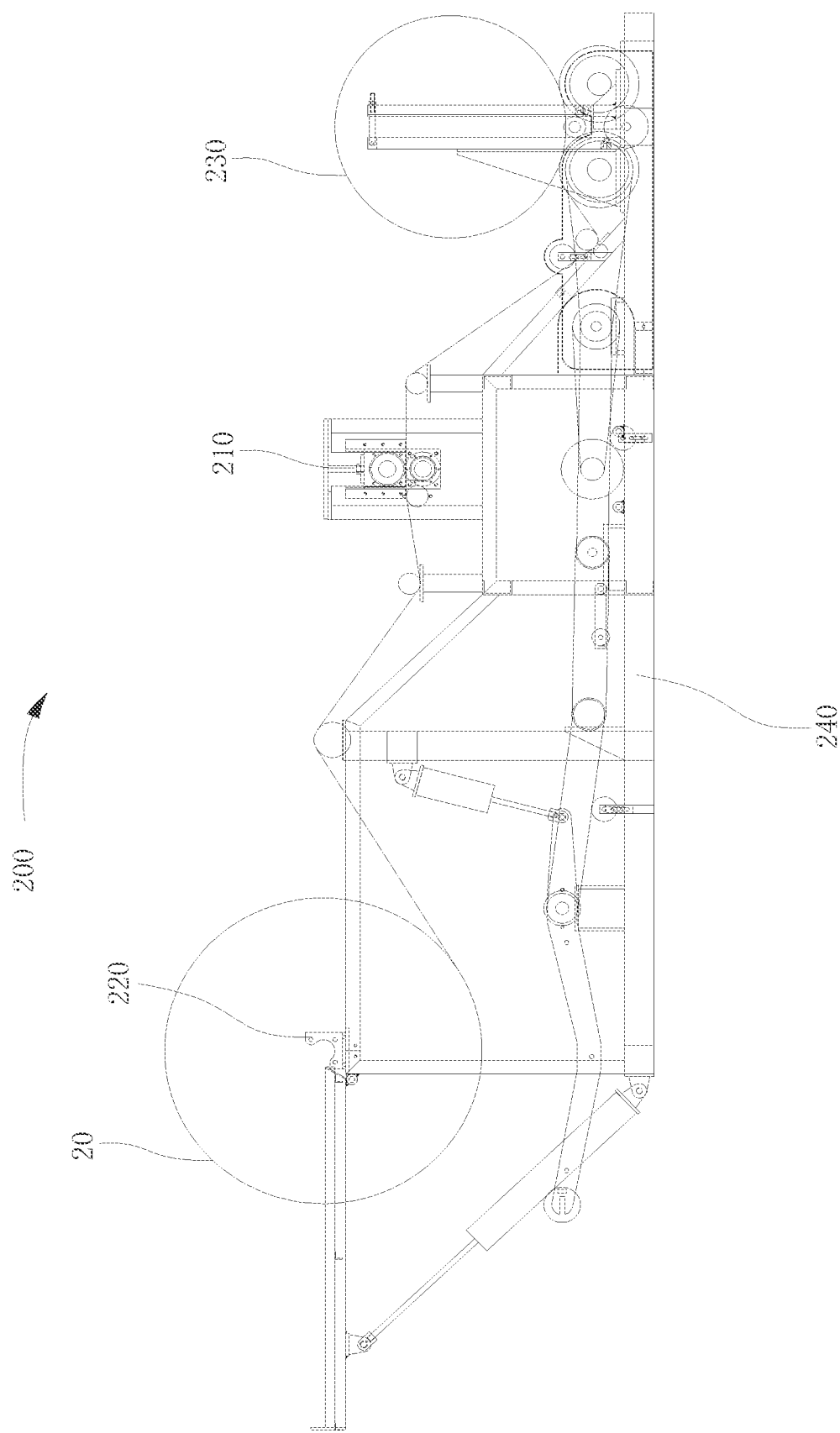
FIG. 2 is a schematic view showing a slitting mechanism of the production system of FIG. 1 and mounted with a paper roller.

A production system of a water-absorbent core according to an embodiment can be used for producing a water-absorbent core with a multilayer structure, which can be used as an inner piece of a diaper or an inner piece of a sanitary napkin. As shown in FIGS. 1 and 2, the production system of a water-absorbent core includes a manufacturing mechanism 100 and a slitting mechanism 200.

The manufacturing mechanism 100 is a forming section for the water-absorbent core. The manufacturing mechanism 100 can laminate a mixture of fluff pulp and hot-melt fibers, fluffy cotton, and a super absorbent polymer (i.e., SAP) to form a mixture layer of fluff pulp and a hot melt and a layer of super absorbent polymer on the fluffy cotton. The number of layers of the mixture layer of fluff pulp and hot-melt fibers is at least two, and the number of layers of the super absorbent polymer layer is at least one, and each layer of the super absorbent polymer is sandwiched between two mixture layers of fluff pulp and hot-melt fibers to obtain a laminate. The manufacturing mechanism 100 can be used to perform a hot air penetration treatment on the laminate to shape the laminate. The mixture layer of the fluff pulp and the hot-melt fibers is a flow guiding layer; and the super absorbent polymer layer serves as a water-absorbent layer.

Referring to FIG. 1 again, the manufacturing mechanism 100 includes a transmission component 110, a supplying component 120, a supplying component 130, a feeding component 140, a vacuum adsorption device 150, and a hot air penetration device 160.

The transmission component 110 is a conveying member of the manufacturing mechanism 100. The transmission component 110 includes a transmission net 112, a transporting net 114, and a vacuum transfer device 116.

The transmission net 112 is a load bearing and conveying member when a mixture of fluff pulp and hot-melt fibers, fluffy cotton, and super absorbent polymer are laminated to form a laminate.

The transporting net 114 is located at the end of the transmission net 112. The transporting net 114 has a conveying direction which is the same as a conveying direction of the transmission net 112.

The vacuum transfer device 116 is disposed between the transmission net 112 and the transporting net 114. The vacuum transfer device 116 is used to convey the laminate on the transmission net 112 to the transporting net 114. In particular, the vacuum transfer device 116 is a vacuum adsorption device, the vacuum transfer device 116 is used to absorb the laminate on the transmission net 112 to the transporting net 114.

The supplying component 120 is configured to convey fluffy cotton to a starting end of a transmitting direction of the transmission component 110. In particular, the supplying component 120 is configured to convey fluffy cotton to a starting end of a conveying direction of the transmission net 112.

More specifically, the supplying component 120 can fluff up the chemical fibers into fluffy cotton, card the fluffy cotton, and convey the carded fluffy cotton to the transmission net 112. The supplying component 120 includes an releasing device 121, a fluffing device 123, a carding device 125, and a fan 126.

The releasing device 121 is configured to loosen the agglomerated chemical fibers. The releasing device 121 is a vibration releaser.

Specifically, the chemical fiber includes polyester fiber, polypropylene fiber and polyethylene fiber; in the chemical fiber, the mass percentage of the polyester fiber is about 3% to about 70%; the total mass percentage of the polypropylene fiber and the polyethylene fiber is about 30%~about 97%; and the mass ratio of polypropylene fiber to polyethylene fiber is 2 to 5:5 to 8.

The fluffing device 123 is connected to the releasing device 121. The fluffing device 123 can fluff the chemical fibers up to form a fluffy cotton, the releasing device 121 can convey the chemical fibers in the releasing device 121 to the releasing device 123. Specifically, the releasing device 121 is provided with a conveyor belt (not shown) that can convey the chemical fibers in the releasing device 121 to the fluffing device 123.

Further, the fluffing device 123 includes a rough fluffer 123a and a fine fluffer 123b, the rough fluffer 123a and the fine fluffer 123b are connected, and the rough fluffer 123a is connected to the releasing device 121. The chemical fibers in the releasing device 121 can be conveyed to the rough fluffer 123a. The chemical fibers are sequentially subjected to rough fluffing and fine fluffing, so that the length of the fluffy cotton is 38 mm to 64 mm, and the specification is about 1.5D to about 35D (where about 1.5D to about 35D indicates that the weight of the 9000 meter fiber is about 1.5 g to about 35 g). More specifically, the rough fluffer 123a and the fine fluffer 123b are connected through a pipe.

The carding device 125 is connected to the fluffing device 123, the carding device 125 is configured to card the fluffy cotton and to convey the carded fluffy cotton to the transmission net 112 of the transmission component 110.

In particular, the carding device 125 is also configured to quantify the outputted fluffy cotton.

Further, the supplying component 120 further includes a conveyor belt 127 that can convey the carded fluffy cotton to the transmission net 112. The conveyor belt 127 is located at the starting end of the transmission net 112. Specifically, one end of the conveyor belt 127 is connected to the carding device 125 and the other end extends to the starting end of the conveying direction of the transmission net 112.

Further, the supplying component 120 also includes a cotton box 128, which is respectively connected to the fluffing device 123 and the carding device 125 through a pipe, and the fluffy cotton discharged from the fluffing device 123 can enter the cotton box 128 to be temporarily stored and then enter the carding device 125. More specifically, the cotton box 128 is connected to the fine fluffer 123b and the carding device 125 via pipes, respectively.

The fan 126 is configured to provide a wind force to convey the fluffy cotton into the carding device 125 from the fluffing device 123. Specifically, the fan 126 is a plural, and a fan 126 is provided on a pipe between the rough fluffer 123a and the fine fluffer 123b, on a pipe between the fine fluffer 123b and the cotton box 128, and on a pipe between the cotton box 128 and the carding device 125, such that the chemical fibers can pass through the rough fluffer 123a and the fine fluffer 123b sequentially, and the fluffy cotton can enter the carding device 125 from the fine fluffer 123b through the cotton box 128.

Further, the supplying component 120 further includes an releaser 129, the releaser 129 is connected to the releasing device 121, and the chemical fibers enter the releasing device 121 through the releaser 129.

The supply component 130 is configured to convey the mixture of fluff pulp and hot-melt fibers to the transmission component 110. The supply component 130 has a plurality of outlets 131, and the plurality of outlets 131 are located in the middle portion of the transmission component 110. Specifically, the plurality of outlets 131 are located above the middle of the transmission net 112 to enable the supply component 130 to convey the mixture of fluff pulp and hot-melt fibers to the transmission net 112; the plurality of outlets 131 are arranged alternately along the conveying direction of the transmission net 112.

Specifically, in the mixture of the fluff pulp and the hot-melt fibers, the mass percentage of the fluff pulp and the hot-melt fibers is about 70% to about 90%:about 10% to about 30%.

Figure 3:
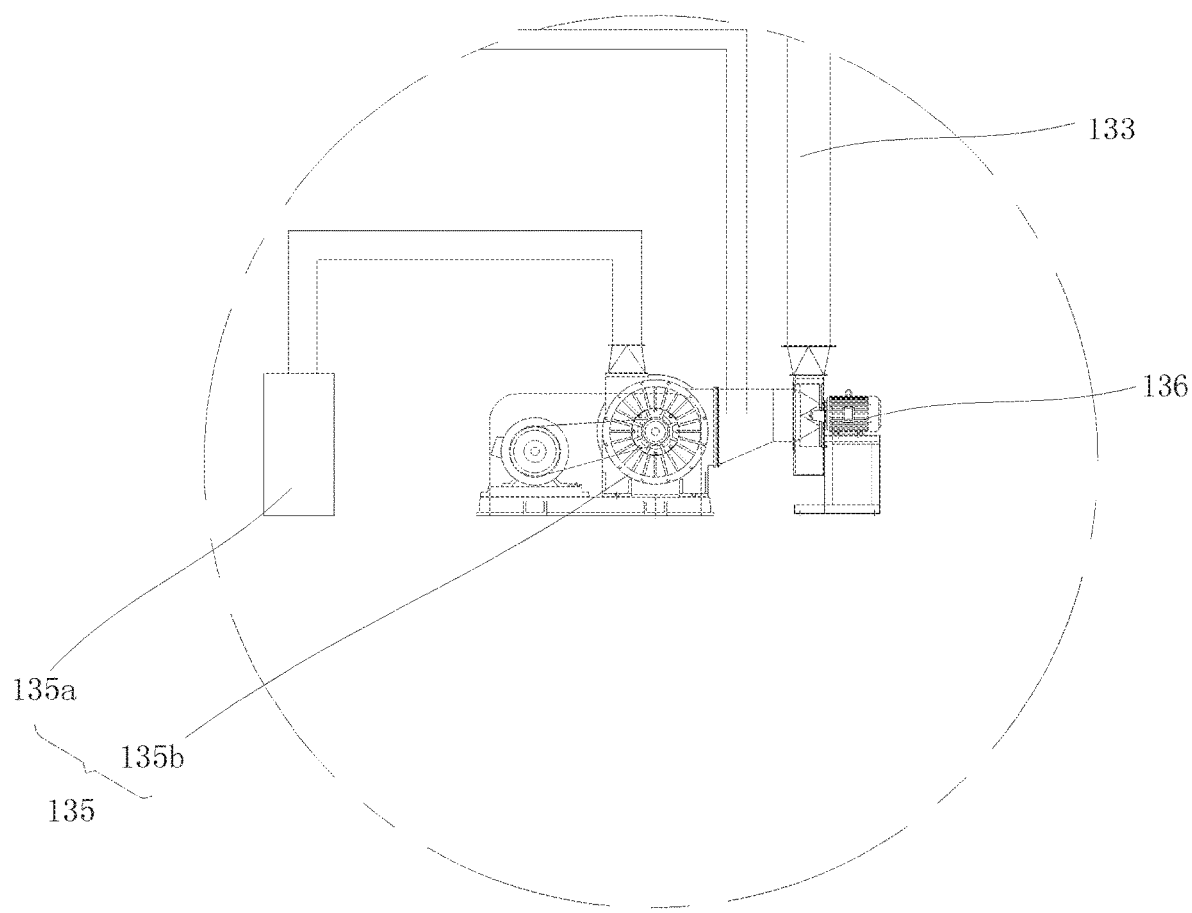
FIG. 3 is an enlarged view of a portion I of the manufacturing mechanism of FIG. 1.

Further referring to FIG. 3, in particular, the supply component 130 includes a conveying device 132, a feeding pipe 133, a storage device 134, a pulverizing device 135, and an air blowing device 136.

The conveying device 132 is configured to mix a fluff pulp and heat-melt fibers to form the mixture of the fluff pulp and the hot-melt fibers. The outlets 131 are located on the conveying device 132, and the mixture of the fluff pulp and the hot-melt fibers in the conveying device 132 can be output from the outlets 131. Specifically, the conveying device 132 is located above the transmission net 112.

Specifically, the conveying device 132 includes a mixing member (not shown) and a duct (not shown) to enable the mixing member to mix the fluff pulp and the hot-melt fibers, and the duct to allow the mixture of the fluff pulp and the hot-melt fibers to be output from the outlets 131.

One end of the feeding pipe 133 is connected to the conveying device 132.

The storage device 134 is configured to store the hot-melt fibers, and the storage device 134 is connected to one end of the feeding pipe 133 away from the outlet 131. The hot-melt fibers include polypropylene fibers and polyethylene fibers; in the hot-melt fibers, the mass ratio of the polypropylene fibers to the polyethylene fibers is 2-5:5-8.

Further, the supply component 130 also includes a fiber collector 137, the fiber collector 137 is respectively connected to the storage device 134 and the end of the feeding pipe 133 away from the conveying device 132. The fiber collector 137 is configured to quantify the hot-melt fibers. The hot-melt fibers in the storage device 134 can reach the feeding pipe 133 through the fiber collector 137. Specifically, the storage device 134 can deliver the hot-melt fibers into the fiber collector 137. It should be understood that the storage device 134 can also carry its own quantitative function, then the fiber collector 137 can be omitted.

The pulverizing device 135 is connected to one end of the feeding pipe 133 away from the outlets 131 and is configured to pulverize the fluff pulp.

Specifically, the pulverizing device 135 includes a rough pulverizer 135a and a fine pulverizer 135b that are connected to each other, and the fine pulverizer 135b is connected to one end of the feeding pipe 133 away from the conveying device 132. The rough pulverizer 135a can pulverize the fluff pulp for a first time, and the fine pulverizer 135b can pulverize the fluff pulp after the first pulverization for a second time. The pulverized fluff pulp has a diameter of about 2.5 mm to about 8 mm; the fluff pulp is straw pulp or wood pulp, preferably wood pulp as the straw pulp is less effective in terms of flow guiding effect due to shorter fibers, and the fibers in the wood pulp are longer and has a better flow guiding effect.

The air delivery device 136 can provide a wind force to convey the hot-melt fibers in the storage device 134 into the delivery device 132 via the feeding pipe 133 and, after the pulverizing device 135 and into the conveying device 132 via the feeding pipe 133. Specifically, under the effect of the wind force of the air blowing device 136, the hot-melt fibers can be conveyed from the fiber collector 137 to the conveying device 132 through the feeding pipe 133; the fluff pulp can be conveyed to the conveying device 132 through the rough pulverizer 135a, the fine pulverizer 135b and the feeding pipe 133 in turn. In the illustrated embodiment, the air blowing device 136 is a fan.

Specifically, the air blowing device 136 is installed at a junction of the feeding pipe 133 and the discharge port 134b.

More specifically, the conveying device 132, the pulverizing device 135, the storage device 134 and the feeding pipe 133 are all plural, and one conveying device 132, one pulverizing device 135, one storage device 134 and one feeding pipe 133 constitute a feeding unit. Each of the delivery devices 132 has an outlet 131. The supply component 130 includes a plurality of feeding units 132, the plurality of conveying devices 132 are all located in the middle portion of the transmission component 110. The number of the fiber collectors 137 is equal to the number of the storage devices 134, and one fiber collector 137 corresponds to one storage device 134.

It should be understood that, the supplying component 130 is not limited to the above-mentioned manner where a plurality of feeding units are provided. For example, the pulverizing device 135, the storage device 134, and the feeding pipe 133 may also be singular. In this case, the conveying device 132 is plural; or there are a plurality of feeding units, some of the feeding units have one conveying device 132, while others of the feeding units have at least two conveying devices 132; or, the pulverizing device 135, the storage device 134, the feeding pipe 133 and the conveying device 132 are all singular, and the delivery device 132 is provided with a plurality of outlets 131.

The feeding component 140 is configured to convey a super absorbent polymer onto the transmission component 110. The feeding component 140 has a plurality of feeding ports 142 and a plurality of outlets 131 arranged alternately along the transmitting direction of the transmission component 110. Each feeding port 142 is located between two of the outlets 131 so as to enable that super absorbent polymer layer to be sandwiched between two layers of mixture of fluff pulp and hot-melt fibers. Specifically, the feeding port 142 is located above the middle of the transmission net 112 to enable the feeding component 140 to convey the super absorbent polymer to the transmission net 112; the plurality of feeding ports 142 and the plurality of outlets 131 are arranged alternately along the conveying direction of the transmission net 112. The plurality of feeding port 142 and the plurality of conveying devices 132 are arranged alternately along the conveying direction of the transmission net 112, each feeding port 142 is located between two of the conveying devices.

The transmission net 112 is configured to drive the mixture of the fluff pulp and the hot-melt fibers, the fluffy cotton, and the super absorbent polymer to move in the conveying direction of the transmission net 112, such that the mixture of the fluff pulp and the hot-melt fibers, and the polymeric water-absorbent resin are laminated on the fluffy cotton to form a laminate.

The super absorbent polymer has a particle size of 20 mesh to 300 mesh. The thickness of the water-absorbent core and the density of the super absorbent polymer in the water-absorbent core will be affected either the particle diameter is too large or too small.

Further, the number of the outlets 131 is one more than the number of the feeding ports 142, and a feeding port 142 is provided between every two outlets 131, so that each layer of the super absorbent polymer layer is sandwiched between the two layers of the mixture of fluff pulp and hot-melt fibers.

Specifically, in the illustrated embodiment, there are three outlets 131 and two feeding ports 142, and there are three conveying devices 132. It can be understood that, the number of the outlets 131 of the conveying device 132 and the number of the feeding ports 142 can be adjusted according to the number of layers of the water-absorbent core body to be produced.

Further, the manufacturing mechanism 100 further includes a pre-compression component 170 disposed on the transmission net 112 and located between the outlet 131 and the feeding port 142 closest to the conveyor belt 127, the pre-compression component 170 is provided with two rotatable rollers (not shown), the two rollers are arranged opposite to each other on both sides of the transmission net 112, and the transmission net 112 is slidably engaged between the two rollers such that the fluffy cotton laminated with the mixture layer of fluff pulp and hot-melt fibers was roll-pressed prior to the addition of the super absorbent polymer.

The vacuum adsorption device 150 is disposed adjacent to the transmission component 110. The position of the vacuum adsorption device 150 corresponds to the position of the plurality of outlets 131, and the vacuum adsorption device 150 can absorb the mixture of the fluff pulp and the hot-melt fibers on the transmission component 110. Specifically, the vacuum adsorption unit 150 is disposed adjacent to the transmission net 112 to enable the vacuum adsorption unit 150 to absorb the mixture of fluff pulp and hot-melt fibers onto the transmission net 112.

Specifically, the vacuum adsorption device 150 is provided with a plurality of vacuum adsorption stages 152, each of which corresponds to an outlet 131, and the transmission net 112 is slidably disposed on the plurality of vacuum adsorption stages 152, thereby facilitating fluff pulp and heat fusion to be better absorbed.

The hot air penetration device 160 is disposed adjacent to the terminal end of the transmission component 110, and the hot air penetration device 160 can perform a hot air penetration treatment to the laminate to shape the laminate, the transmission component 110 can convey the laminate into the hot air penetration device 160. Specifically, the transmission component 110 extends through the hot air penetration device 160 to enable the transmission component 110 to convey the laminate into the hot air penetration device 160. The layers of the laminate are joined together by subjecting the laminate to a hot air penetration treatment to melt the hot-melt fibers. More specifically, the transporting net 114 extends through the hot air penetration device 160 to enable the transporting net 114 to convey the laminate into the hot air penetration device 160.

The temperature at which the laminate is subjected to hot air penetration is 120° C. to 150° C.

Further, the manufacturing mechanism 100 also includes a squeezing component 180 arranged adjacent to the terminal end of the transporting net, the squeezing component includes two rollers 182 arranged opposite to each other on both sides of the transporting net 114, and the transporting net 114 is slidably engaged between the two rollers 182 such that the two rollers 182 can roll-press the laminate after the hot air penetration treatment and thereby adjusting the thickness of the laminate. Since the laminate is outputted from the hot air penetration device 160 with residual heat, such that the thickness of the laminate can be adjusted by passing the laminate through the squeezing component 180 without re-heating.

Specifically, the pressure at which the squeezing component 180 roll-presses the laminate after the hot air penetration treatment is 0.3 MPa to 0.8 MPa.

Referring again to FIG. 2, the slitting mechanism 200 includes an ultrasonic cutting device 210 configured to ultrasonically cut the laminate after the hot air penetration treatment and fuse hot-melt fibers at a cut portion of the laminate to form the water-absorbent core. By way of the ultrasonic cutting, each of the mixed layers of the laminate can be fused by the hot-melt fibers at the cut portions under the effect of ultrasonic waves, thereby increasing the connectivity between the mixed layers and as well as operating to seal the edge.

Specifically, the process parameters of the ultrasonic cutting device 210 for cutting the hot air through-processed laminate are: cutting speed at 80 m/min to 250 m/min, and ultrasonic frequency at more than 20,000 Hz. The cutting speed is matched with the ultrasonic frequency to ensure the quality of the cutting and a favorable edge sealing effect.

Further, the production part 100 also includes a winder 190 configured to roll up the shaped laminate to form a roll paper 20, the slitting mechanism 200 further includes a fixing member 220 and a rolling device 230, the fixing member 220, the ultrasonic cutting device 210, and the rolling device 230 are arranged in sequence, and the fixing member 220 is configured to mount the roll paper 20, and the rolling device 230 is configured to roll up the laminate after cutting (i.e., the water-absorbent core), such that the rolling device 230 can drive the roll paper 20 to rotate on the fixing member 220, and enable the laminate to enter the ultrasonic cutting device 210 for cutting.

Further, the slitting mechanism 200 further includes a fixing bracket 240, the fixing member 220 is rotatably fixed on the fixing bracket 240. The ultrasonic cutting device 210 and the rolling device 230 are both mounted on the fixing bracket 240, and the ultrasonic cutting device 210 is fixed between the fixing member 220 and the rolling device 230.

The process for producing the water-absorbent core of the foregoing production system 100 will be described as follows:

The chemical fibers are conveyed to the releaser 129, and the releaser 129 conveys the chemical fibers to the releasing device 121 for vibration fluffing, and the releasing device 121 conveys the chemical fibers after vibrate-fluffing to the rough fluffer 123a for rough fluffing. Under the effect of the fan 126, the chemical fibers after rough fluffing by the rough fluffer 123a enters into the fine fluffer 123b for fine fluffing to obtain fluffy cotton; then under the effect of the fan 126, the fluffy cotton enters the carding device 125 for quantification and carding, and the carded fluffy cotton is conveyed by the conveyor belt 127 to the starting end of the transmission net 112.

The hot-melt fibers are discharged from the storage device 134 into the fiber collector 137 and are outputted after quantification, and then into the conveying device 132 via the feeding pipe 133 under the effect of the wind force provided by the air blowing device 136. the fluff pulp enters into the fine pulverizer 135b from the rough pulverizer 135a for further pulverization, and enters the conveying device 132 through the feeding pipe 133. The conveying device 132 mixes the hot-melt fibers and the fluff pulp to formulate a mixture of fluff pulp and hot-melt fibers. The mixture of fluff pulp and hot-melt fibers is further conveyed from the outlet 131 to the transmission net 112, under the suction effect of the vacuum adsorption device 150, the pulverescent mixture of fluff pulp and hot-melt fibers is absorbed on the transmission net 112. The super absorbent polymer is conveyed to the transmission net 112 through the feeding port 142.

Since the conveyor belt 127 is located at the starting end of the transmission net 112, the outlets 131 and the feeding ports 142 of the plurality of conveying devices 132 are located above the middle of the transmission net 112. The outlets 131 and the feeding ports 142 are arranged alternately along the conveying direction of the transmission net 112. Each feeding port 142 is located between the outlets 131 of two of the conveying devices 132. Under the conveying effect of the transmission net 112, the fluffy cotton moves along with the transmission net 112, the mixture of hot-melt fibers and fluff pulp from the outlet 131 of the conveying device 132 will drop on the fluffy cotton when passing through the outlet 131 closest to the conveying belt 127 and is absorbed on the fluffy cotton to form a flow guiding layer. Then the roller of the pre-compression component 170 pre-roll-presses the fluffy cotton laminated with the flow guiding layer. When the fluffy cotton laminated with the flow guiding layer arrives at the feeding port 142, the super absorbent polymer drops onto the flow guiding layer on the fluffy cotton to form a water-absorbent layer. Then, when passing through the outlet 131 of the second feeding device 132, the mixture of the hot-melt fibers and the fluff pulp will drop again onto the water-absorbent layer and a flow guiding layer is formed again. The laminate is then obtained by a layer of water-absorbent layer and a layer of flow guiding layer and over again. Since each feeding port 142 is located between the outlets 131 of two of the conveying devices 132, there is one feeding port 142 between the outlets 131 of every two conveying devices 132. As such, each absorbent layer of the laminate is located between two flow guiding layers.

When the laminate moves to the end of the transmission net 112 along with the transmission net 112, the vacuum transfer device 116 absorbs the laminate on the transmission net 112 onto the transporting net 114.

The laminate then moves along with the transporting net 114 and enters the hot air penetration device 160 for hot air penetration to shape the laminate, and the hot hair penetration treated laminate with residual heat is roll-pressed by the two rollers 182 of the squeezing component 180 to adjust the thickness of the laminate, and the laminate after roll-pressing by the paper roller 190 is rolled up to form a roll paper;

The roll paper is mounted on the fixing member 220, one end of the laminate is pulled, the roll paper starts to rotate, and the laminate enters the ultrasonic cutting device 210 for ultrasonic cutting to form a water-absorbent core, and the water-absorbent core body enters the rolling device 230 and is rolled up. Under the rolling effect of the rolling device 230, the laminate is pulled and rotating, such that the laminate continuously passes through the ultrasonic cutting device 210 for ultrasonic cutting.

The foregoing production system of a water-absorbent core has at least the following advantages:

Since the supplying component 120 of the production system can convey fluffy cotton to the starting end of the transmission component 110, the plurality of outlets 131 of the supplying component 130 configured to convey the mixture of fluff pulp and hot-melt fibers onto the transmission component 110 are located in the middle of the transmission component 110, the plurality of feeding ports 142 of the feeding component 140 configured to convey the super absorbent polymer to the transmission component 110 and the plurality of outlets 131 are arranged alternately along the transmitting direction of the transmission component 110, and each feeding port 142 is located between two of the outlets 131, and the vacuum adsorption device 150 is disposed adjacent to the transmission component 110. The position of the vacuum adsorption device 150 corresponds to the positions of the plurality of outlets 131 such that the mixture of the fluff pulp and the hot-melt fibers can be absorbed on the transmission component 110 such that, with the conveying effect of the transmission component 110, the mixture of the hot-melt fibers and the fluff pulp output from the outlet 131 and the super absorbent polymer output from the feeding port 142 can drop onto the fluffy cotton conveyed at the starting end of the transmission component to form a laminate according to the arrangement sequence of the outlets 131 and the feeding ports 142. The mixture of the pulverizent hot-melt fibers and fluff pulp outputted from the outlet 131 can be absorbed on the fluffy cotton on the transmission component 110 under the suction of the vacuum adsorption device 150. Each super absorbent polymer layer of the formed laminate is sandwiched between two layers of the mixture of the hot-melt fiber sand fluff pulp. The laminate is further conveyed by the transmission component 100 to the hot air penetration device 160 to perform hot air penetration treatment to the laminate to melt the hot-melt fibers, thereby bonding the fluffy cotton, each super absorbent polymer layer, each hot-melt fibers and fluff pulp mixture layer together to shape the laminate. This not only can realize the automatic lamination of layers and the automatic hot air penetration treatment of the laminates, effectively improve the production efficiency and save manpower, but also can connect the layers together well, so that the layers of the absorbent core have better connectivity and the stratification problem caused by water swelling of the absorbent resin is reduced. Since the fluff pump in each layer of the mixture of the hot-melt fibers and the fluff pulp can provide the flow guide effect, and that each layer of super absorbent polymer is located between two layers of mixture of hot melt fibers and fluff pulp, thereby providing each layer of the mixture of hot-melt fibers and the fluff pulp with a better diffusibility to improve the diffusion and absorption of the water-absorbent core. At the same time, the ultrasonic cutting device 210 of the slitting mechanism 200 cuts the laminate after the hot air penetration treatment to obtain the water-absorbent core, so that not only the laminate can be cut, but also the hot-melt fibers of each layer of the laminate can be fused again. Thereby further increasing the connectivity between the layers of the water-absorbent core and functioning as an edge seal while cutting.

The different technical features of the above embodiments can have various combinations which are not described for the purpose of brevity. Nevertheless, to the extent the combining of the different technical features do not conflict with each other, all such combinations must be regarded as being within the scope of the disclosure.

The foregoing implementations are merely specific embodiments of the present disclosure, and are not intended to limit the protection scope of the present disclosure. It should be noted that any variation or replacement readily figured out by persons skilled in the art within the technical scope disclosed in the present disclosure shall all fall into the protection scope of the present disclosure. Therefore, the protection scope of the present disclosure shall be subject to the protection scope of the claims.

What is claimed is:

1. A production system of a water-absorbent core, comprising: a manufacturing mechanism and a slitting mechanism, the manufacturing mechanism comprising a transmission component, a conveying component, a supplying component, a feeding component, a vacuum adsorption device, and a hot air penetration device, wherein:

the supplying component is configured to convey fluffy cotton to a starting end of the transmission component;

the conveying component is configured to convey a mixture of fluff pulp and hot-melt fibers to the transmission component, the conveying component has a plurality of outlets, and the plurality of outlets are located in a middle portion of the conveying component;

the feeding component is configured to convey a super absorbent polymer to the transmission component, the feeding component has a plurality of feeding ports, the plurality of feeding ports and the plurality of outlets are arranged alternately along a transmitting direction of the transmission component, and each said feeding port is located between two of the outlets;

the transmission component is configured to drive the mixture of the fluff pulp and the hot-melt fibers, the fluffy cotton, and the super absorbent polymer to move in the transmitting direction of the transmission component, such that the mixture of the fluff pulp and the hot-melt fibers, and the super absorbant polymer are laminated on the fluffy cotton to form a laminate, and the transmission component is further configured to convey the laminate into the hot air penetration device;

the vacuum adsorption device is disposed adjacent to the transmission component, and a position of the vacuum adsorption device corresponds to a position of the plurality of outlets, such that the mixture of fluff pulp and hot-melt fibers can be absorbed on the transmission component;

the hot air penetration device is disposed adjacent to a terminal end of the transmission component, and the hot air penetration device is configured to perform a hot air penetration treatment to the laminate; and the slitting mechanism comprises an ultrasonic cutting device configured to ultrasonically cut the laminate after the hot air penetration treatment and fuse the hot-melt fibers at a cut portion of the laminate.

2. The system according to claim 1, wherein in the mixture of the fluff pulp and the hot-melt fibers, the mass percentage of the fluff pulp is about 70% to about 90%.

3. The system according to claim 1, wherein the hot-melt fibers comprise polypropylene fibers and polyethylene fibers; wherein the mass ratio of the polypropylene fibers to the polyethylene fibers is 2 to 5:5 to 8.

4. The system according to claim 1, wherein the transmission component comprises:

a transmission net, the plurality of the outlets and the plurality of feeding ports are both located above a middle portion of the transmission net and are arranged alternately along a conveying direction of the transmission net, and the conveying component is configured to convey the mixture of fluff pulp and hot-melt fibers to the transmission net, the feeding component is configured to convey the super absorbant polymer to the transmission net, the supplying component is configured to convey the fluffy cotton to a starting end of the transmission net, and the vacuum adsorption device is configured to adsorb the mixture of the fluff pulp and the hot-melt fibers on the transmission net;

a transporting net located at an end of the transmission net, a conveying direction of the transporting net is the same as the conveying direction of the transmission net, and the transporting net extends through the hot air penetration device, such that the transporting net is configured to convey the laminate into the hot air penetration device; and a vacuum transfer device disposed between the transmission net and the transporting net, the vacuum transfer device is configured to transfer the laminate on the transmission net to the transporting net.

5. The system according to claim 4, wherein the supplying component comprises a conveyor belt configured to convey the fluffy cotton onto the transmission net, the conveyor belt is located at the starting end of the transmission net.

6. The system according to claim 5, wherein the manufacturing mechanism further comprises a pre-compression component disposed on the transmission net and located between the outlet and the feeding port closest to the conveyor belt, the pre-compression component has two rotatable rollers arranged opposite to each other on both sides of the transmission net, and the transmission net is slidably engaged between the two rollers of the pre-compression component.

7. The system according to claim 4, wherein the manufacturing mechanism further comprises a squeezing component arranged adjacent to a terminal end of the transporting net, the squeezing component comprises two rollers arranged opposite to each other on both sides of the transporting net, and the transporting net is slidably engaged between the two rollers of the squeezing component, such that the two rollers roll-press the laminate after the hot air penetration treatment.

8. The system according to claim 1, wherein the number of the outlets is one more than the number of the feeding ports.

9. The system according to claim 1, wherein the supplying component comprises a releasing device, a fluffing device, a carding device and a fan, the releasing device is configured to release agglomerated chemical fibers, the fluffing device is configured to convey the chemical fibers from the releasing device into the fluffing device and fluff the chemical fibers up to form the fluffy cotton, the carding device is configured to card the fluffy cotton, and convey the carded fluffy cotton to the transmission component, and the fan is configured to provide a wind force such that the fluffy cotton enters the carding device from the fluffing device.

10. The system according to claim 9, wherein the fluffing device comprises a rough fluffer and a fine fluffer, the chemical fibers in the releasing device are conveyed to the rough fluffer; wherein the chemical fibers are sequentially subjected to rough fluffing by the rough fluffer and fine fluffing by the fine fluffer.

11. The system according to claim 10, wherein the length of the fluffy cotton is about 38 mm to about 64 mm, and the specification is about 1.5D to about 35D.

12. The system according to claim 9, wherein the supplying component further comprises a cotton box connected to the fluffing device and the carding device through a pipe, respectively, and the fluffy cotton discharged from the fluffing device enters the cotton box to be temporarily stored and then enters the carding device.

13. The system according to claim 9, wherein the supplying component further comprises a releaser connected to the releasing device, the chemical fibers enter the releasing device through the releaser.

14. The system according to claim 1, wherein the conveying component comprises:

a conveying device configured to mix a fluff pulp and heat-melt fibers to form the mixture of the fluff pulp and the hot-melt fibers, wherein the plurality of outlets is located on the conveying device;

a feeding pipe connected to the conveying device at an end thereof;

a storage device connected to an end of the feeding pipe away from the plurality of outlets and configured to store the heat-melt fibers;

a pulverizing device connected to the end of the feeding pipe away from the plurality of outlets and configured to pulverize the fluff pulp; and an air blowing device configured to provide a wind force to convey the heat-melt fibers in the storage device into the conveying device via the feeding pipe, and convey the fluff pulp pulverized by the pulverizing device into the conveying device via the feeding pipe;

wherein the mixture of the fluff pulp and the heat-melt fibers in the conveying device is output from the plurality of outlets.

15. The system according to claim 14, wherein the conveying component further comprises a fiber collector configured to quantify the hot-melt fibers, the fiber collector is respectively connected to the storage device and the end of the feeding pipe away from the conveying device.

16. The system according to claim 14, wherein the conveying device comprises a mixing member and a duct to enable the mixing member to mix the fluff pulp and the hot-melt fibers, and the duct to allow the mixture of the fluff pulp and the hot-melt fibers to be output from the plurality of outlets.

17. The system according to claim 14, wherein the pulverizing device comprises a rough pulverizer configured to pulverize the fluff pulp for a first time and a fine pulverizer configured to pulverize the fluff pulp for a second time after the first time pulverization, wherein the rough pulverizer and the fine pulverizer are connected to each other.

18. The system according to claim 14, wherein the pulverized fluff pulp has a diameter of about 2.5 mm to about 8 mm.

19. The system according to claim 14, wherein the conveying device, the feeding pipe, the storage device, the pulverizing device, and the air blowing device are plural, one conveying device, one feeding pipe, one storage device, one pulverizing device, and one air blowing device constitute a feeding unit, and each conveying device has one outlet.

20. The system according to claim 1, wherein the manufacturing mechanism further comprises a paper roller configured to roll up the laminate after hot air penetration treatment to form a roll paper, and the slitting mechanism further comprises a fixing member and a rolling device, the fixing member, the ultrasonic cutting device and the rolling device are arranged in sequence, and the fixing member is configured to mount the roll paper, and the rolling device is configured to roll the laminate after cutting, such that the rolling device drives the roll paper to rotate on the fixing member, and enable the laminate to enter the ultrasonic cutting device for cutting.

* * * * *